United States Patent [19]

Wong

[11] Patent Number: 4,961,931

[45] Date of Patent: Oct. 9, 1990

[54] METHOD FOR THE MANAGEMENT OF HYPERPLASIA

[75] Inventor: Patrick S.-L. Wong, Palo Alto, Calif.

[73] Assignee: Alza Corporation, Palo Alto, Calif.

[21] Appl. No.: 242,249

[22] Filed: Sep. 9, 1988

Related U.S. Application Data

[60] Continuation-in-part of Ser. No. 895,611, Aug. 11, 1986, abandoned, which is a continuation-in-part of Ser. No. 714,421, Mar. 21, 1985, Pat. No. 4,629,449, which is a division of Ser. No. 402,953, Jul. 29, 1982, abandoned.

[51] Int. Cl.$^5$ .......................................... A61K 31/505
[52] U.S. Cl. ..................................... 424/430; 424/431; 424/432; 424/433; 604/54; 604/55; 604/56; 604/285; 604/288
[58] Field of Search ................................ 424/430-433; 604/54-56, 893, 285, 288

[56] References Cited

U.S. PATENT DOCUMENTS

| | | | |
|---|---|---|---|
| 3,733,407 | 5/1973 | Segre | 424/239 |
| 3,797,492 | 3/1974 | Place | 128/260 |
| 3,828,781 | 8/1974 | Rothman | 128/278 |
| 3,896,819 | 7/1975 | Zaffaroni et al. | 128/130 |
| 3,911,911 | 10/1975 | Scommenga | 128/130 |
| 3,920,805 | 11/1975 | Roseman | 424/15 |
| 3,938,515 | 2/1976 | Leeper et al. | 128/260 |
| 3,967,618 | 7/1976 | Zaffaroni | 128/130 |
| 3,991,760 | 11/1976 | Drobish et al. | 128/260 |
| 3,995,633 | 12/1976 | Gougeon | 128/260 |
| 3,995,634 | 12/1976 | Drobish | 128/260 |
| 4,145,416 | 3/1979 | Lachnit-Fixson et al. | 424/238 |
| 4,155,991 | 5/1979 | Schopflin et al. | 424/15 |
| 4,198,634 | 4/1980 | Jernigan et al. | 343/100 CL |
| 4,198,976 | 4/1980 | Drobish et al. | 128/260 |
| 4,200,098 | 4/1980 | Ayer et al. | 128/260 |
| 4,215,691 | 8/1980 | Wong | 128/260 |
| 4,237,885 | 12/1980 | Wong et al. | 128/260 |
| 4,256,236 | 5/1981 | Pacella | 128/203.23 |
| 4,285,987 | 8/1981 | Ayer et al. | 427/3 |
| 4,286,587 | 9/1981 | Wong | 128/127 |
| 4,292,965 | 10/1981 | Nash et al. | 128/260 |
| 4,315,925 | 2/1982 | Hussain et al. | 424/239 |
| 4,326,510 | 4/1982 | Buckles | 128/127 |
| 4,372,951 | 2/1983 | Vorys | 424/239 |
| 4,402,695 | 9/1983 | Wong | 604/892 |
| 4,425,339 | 1/1984 | Pitchford | 424/239 |
| 4,596,576 | 6/1986 | de Nijs | 604/892 |
| 4,629,449 | 12/1986 | Wong | 604/55 |

FOREIGN PATENT DOCUMENTS

0136011 4/1985 European Pat. Off. .

OTHER PUBLICATIONS

Kempers, Roger D., "The Menopause", pp. 209–215; *Textbook of Gynecology*, Edited by De Alvarez, M.D., Lea & Febiger, (1977), Philadelphia.

Gambrell, Jr., M.D., R. Don, "The Menopause: Benefits and Risk of Estrogen-Progestogen Replacement Therapy", *Fertility and Sterility*, vol. 37, No. 4, (Apr. 1982), pp. 457–473.

Whitehead, M. I. & Campbell, S., "Endometrial Histology, Uterine Bleeding and Oestrogen Levels in Menopausal Women Receiving Oestrogen Therapy and Oestrogen Progestogen Therapy", pp. 65–80, *Endometrial Cancer*, edited by Brush, M. G., King, R. J. B. & Taylor, R. W., (1977), Bailliere Tindall-London.

King, R. J. B., Whitehead, M. I., Campbell, S. & Minardi, Jane, "Effects of Estrogens and Progestogens on the Biochemistry of the Post-Menopausal Endometrium," pp. 111–119, *The Role of Estrogen/Progestogen in the Management of the Menopause*, Proceedings of a Symposium held at the U. of Sheffield on Mar. 16, 1987, MTP Press, Ltd., Lancaster, England.

Gal, M.D., David, Edman, M.D., Clare D., et al., "Long-Term Effect of Megestrol Acetate in the Treatment of Endometrial Hyperplasia," pp. 316–322, *Am. J. Obstet. Gynecol.*, vol. 146, No. 3, (Jun., 1983).

*Primary Examiner*—Patrick Ryan
*Attorney, Agent, or Firm*—Paul L. Sabatine; Edward Mandell; Steven F. Stone

[57] ABSTRACT

The invention is for a vaginal dispenser comprising a wall surrounding an internal lumen and having a pair of ends with one end placed inside the other end to form a closed dispenser. A vaginally administrable beneficial agent is housed in the lumen for release by the dispenser over time.

2 Claims, 1 Drawing Sheet

METHOD FOR THE MANAGEMENT OF HYPERPLASIA

This application is a continuation-in-part of U.S. patent application Ser. No. 06/895,611 filed Aug. 11, 1986 now abandoned which application Ser. No. 06/895,611 is a continuation-in-part of U.S. patent application Ser. No. 06/714,421 filed on Mar. 21, 1985, now U.S. Pat. No. 4,629,449 issued Dec. 16, 1986 which application 06/714,421 is a division of U.S. patent application Ser. No. 06/402,953 filed July 29, 1982. These applications are assigned to ALZA Corporation of California and are incorporated herein by reference and benefit is claimed of their filing dates.

FIELD OF THE INVENTION

This invention pertains to a vaginal dispenser. Specifically, the invention relates to an intravaginal dispenser housing a vaginally dispensable drug for dispensing drug to a vagina over a prolonged period of time. More specifically, the invention also concerns a method for treating a warm-blooded host to produce a beneficial result in the management of health and disease.

BACKGROUND OF THE INVENTION

Vaginal devices for delivering a drug to a vagina are known to the prior art. For example U.S. Pat. No. 196,979 issued to patentee R. H. Kline discloses medicated-ring device consisting of 2 a fabric filled with a medicinal agent useful for treating vaginal diseases. In Gordon W. Duncan U.S. Pat. No. 3,545,439 there is disclosed an intravaginal ring-shaped device that can be made of various kinds of polymeric materials. The device is formed of a solid polymer containing drug that is released by diffusion to the vagina. The device optionally contains a tension spring for keeping it in the vagina. In Theodore J. Roseman U.S. Pat. No. 3,920,805 discloses a solid polymeric device that has a non-medicated central solid core and an encircling medicated coating on the polymer. The device releases drug by diffusion and, in a preferred embodiment, the device is ring-shaped with a flat tensioning spring molded in the non-medicated central core. A vaginal medicament dispensing means is disclosed by James Lee Drobish and Thomas William Gougeon in U.S. Pat. No. 3,991,760. The device in this patent consists of a plurality of containers having walls releasably containing an active agent and connected by a fin arrangement. A vaginal medicament dispensing device is disclosed in Thomas W. Gougeon. U.S. Pat. No. 3,995,633. The device is characterized by a plurality of containers held in place by a retaining ring by virtue of their bulbous shape. Gisela Schopflen et al. U.S. Pat. No. 4,012,496 issued to discloses a vaginal ring consisting essentially of a supporting medicament-free vaginal ring having an encircling indentation with a smaller vaginal medicament containing a ring in the indentation. Gisela Schopflin et al U.S. Pat. No. 4,155,991 is similar to U.S. Pat. No. 4,012,496 reciting the structure and, additionally, the polymer used for making the vaginal ring. A vaginal contraceptive system is described in Patrick S.-L. Wong. U.S. Pat. No. 4,215,691 The vaginal system comprises a wall surrounding a reservoir housing a drug and a carrier and made of a copolymer. U.S. Pat. No. 4,292,964 issued to Harold A. Nash et al discloses an intravaginal ring consisting essentially of an inner core, a medicated layer encircling the inner core, and an outer layer surrounding the medicated layer. In Patrick S.-L. Wong U.S. Pat. No. 4,286,587 discloses a vaginal device comprising a delivery module with an internal reservoir housing a drug for controlled release to a vagina.

The vaginal devices described above are useful for their intended purposes and they represent a valuable contribution to the vaginal dispensing art. Now it has been discovered a vaginal dispenser can be provided that is easy to manufacture, can be made with materials that are vaginally acceptable and can be used for dispensing drug to the vagina over time. The present invention provides an improvement by making available a vaginal dispenser manufactured as a closed dispenser from the materials comprising the vaginal dispenser. The present invention pertains also to a method for dispensing at least one beneficial agent in the vagina to produce an intended beneficial therapeutic result. The method of the invention provides beneficial agent delivery patterns such as continuous, interrupted, cyclical, sequential, and the like.

BRIEF DESCRIPTION OF THE DRAWINGS

In the drawings, which are not drawn to scale but are set forth to illustrate various embodiments of the invention, the drawing figures are a follows.

In the drawings and in the specification like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
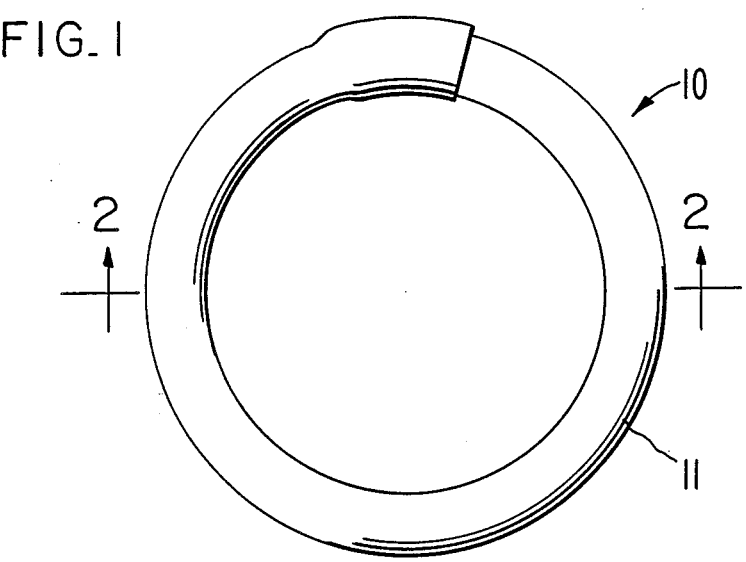
FIG. 1 illustrates an intravaginal dispenser sized, shaped and adapted for easy insertion and comfortable retention in a vagina.

Turning now to the drawings in detail, which are an example of an intravaginal dispenser that can be used for delivering a vaginally acceptable drug to a vagina for carrying out the therapeutic program of the invention, and which example is not to be construed as limiting the invention, one presently preferred embodiment thereof is seen in FIG. 1 and identified by the numeral 10. In FIG. 1, vaginal dispenser 10 comprises a body 11 sized, shaped and adapted for placement in a vagina.

Figure 2:
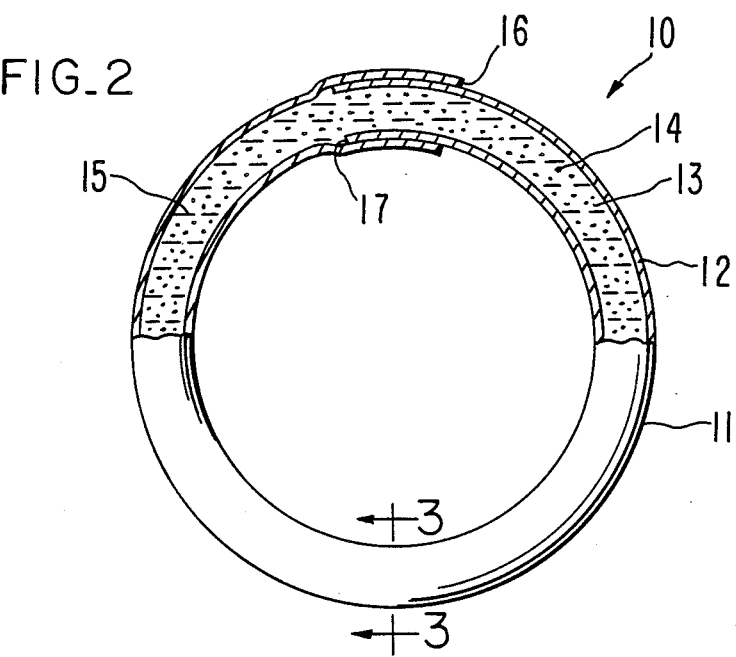
FIG. 2 illustrates the intravaginal dispenser of FIG. 1 seen 2 in opened-section through 2—2 of FIG. 1.

In FIG. 2, vaginal dispenser 10 is seen in opened-section through 2—2 of FIG. 1. In FIG. 2 vaginal dispenser 10 is seen comprising body 11 formed of wall 12 comprising a polymer that releases a vaginally acceptable agent by diffusion, or wall 12 comprises a microporous polymer that releases a vaginally acceptable agent through its pores and, which rate in either manufacture, maintains the prescribed rate of administration of vaginally acceptable, useful agent to the vagina throughout the life of vaginal dispenser 10. In the porous embodiment, the pores in the wall of the dispensing device can be preformed, or the pores can be formed when the device is in operation in the vagina by leaching a pore former such as a sorbitol, lactose, or 2 the like, from the wall of the device. Wall 12 surrounds and forms an internal lumen 13 that is a reservoir for storing beneficial agent 14, represented by dots. Lumen 13 also contains a carrier for agent 14, which carrier is an inner mass transfer conductor for supplying agent 14 to wall 12. Wall 12 surrounds internal lumen 13 comprising a pair of ends, end 16 and end 17, that are joined into a single, integral shaped tubular vaginal dispenser 10. The union is effected by enlarging end 16 for slidably receiving end 17 in mated relation to form an essentially fluid tight union. In another embodiment vaginal dispenser 10 can have at least one of its ends 16 or 17 made smaller than the other end and the smaller end placed in the non-enlarged end to form a closed vaginal dispenser 10.

Figure 3:
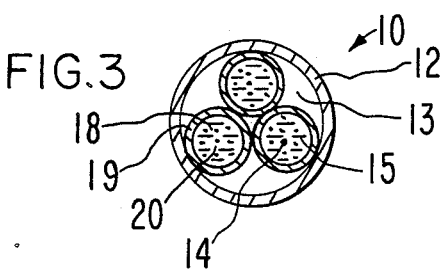
FIG. 3 is a cross-section through 3—3 of FIG. 1 illustrating in opened-section the lumen containing more than one tube for storing and releasing drug.

FIG. 3 is a cross-section through 3—3 of vaginal dispenser 10 of FIG. 3. FIG. 3 comprises wall 12 and lumen 13. Lumen 13 comprises at least one, and in a preferred embodiment more than one, tubes 18 comprising a wall 19 that surrounds an interior space 20 containing beneficial agent 14. The multiplicity of tubes 18 in space 13 can function as a second reservoir for storing and supplying beneficial agent 14 to first reservoir space 13 for release at a controlled rate by wall 12. In another embodiment wall 19 can be a rate controlling wall, and wall 12 can be permeable to fluid but impermeable to bacteria.

Vaginal dispenser 10 can embrace many shapes and in a presently preferred embodiment comprises a single, annular shape, which annular shape includes ring, oval, ellipse, toroidal and like appearing annular shapes. The novel vaginal dispenser 10 can be used for delivering beneficial agent 14 to animals, including warm-blooded mammals, which expression includes humans and primates. Vaginal dispenser 10 also can be used for delivering agent 14 to farm, laboratory, sport and zoo animals. The dimensions of the dispenser will vary depending on the host and the shape for delivering agent 14. For example, at its maximum dimension the dispenser wall measures from one loci on the wall to a distant loci on the wall from 0.4 cm to 16 cm, with presently preferred dispensers exemplified by an annular shaped dispenser which can have an external diameter of from 0.5 cm to 14 cm, with general dimensions for various hosts as follows: humans, 6 cm to 12 cm; sheep, 2 cm to 7 cm; dogs, 0.5 cm to 5.0 cm; swine, 2 cm to 7.5 cm; household cats, 0.4 cm to 4 cm, and dairy cattle, 5 cm to 12 cm.

DETAILED DESCRIPTION OF THE INVENTION

In accordance with the practice of this invention it has now been found vaginal dispenser 10 can be made with vaginally acceptable polymeric materials including polymeric materials that release agent 14 by diffusion and porous polymeric materials that release agent 14 through its pores. The polymeric materials used are substantially free of any adverse affects on the vagina and on the host. The vagina is lined with an extremely delicate tissue and it is essential, therefore, that the materials forming dispenser 10 do not adversely affect the vagina. The materials used for the purpose of this invention are the vaginally compatible material set forth below. By compatible is meant the materials do not break down in the vagina, there is no absorption of the materials, there is no deleterious action on the sensitive tissues in the area of placement and retention of the vaginal dispenser over a prolonged period of time, and the materials do not harm the active agent and the carrier housed in dispenser 10.

The polymers suitable for the purpose of the invention mainly for forming wall 12 and wall 19 include polymers, copolymers, and the like, generically represented by olefin and vinyl-type polymers, carbohydrate-type polymers, condensation-type polymers, addition-type polymers, rubber-type polymers, and organosilicon polymers. In a presently preferred embodiment one group of polymers useful for manufacturing the vaginal dispenser are polymers known as thermoplastic polymers. These polymers are capable of being softened by heating and hardened by cooling through a temperature range characteristic of the polymer and, in the softened state, they can be shaped by flow into devices by molding or extrusion. The change for these materials upon heating is substantially physical. One example of a thermoplastic polymer that can be used for the present purpose is styrene-butadiene block copolymer. The styrene-butadiene block copolymer useful for manufacturing wall 12 and 19 includes those generally formed by initiation at a chain end of an already formed polymeric chain. The block copolymers are thermoplastic elastomers because of their ability to become fluid and moldable at elevated temperatures. These properties lend themselves to the manufacture of system 10. Generally the styrene block copolymer will have a molecular weight in the range of 10,000 to 20,000 and the butadiene will have a molecular weight in the range of 40,000 to 100,000. Additional polymers that can be used for manufacturing dispenser 10 include poly(methylacrylate), poly(butylmethacrylate), plasticized poly(vinylchloride), poly(trifluorochloroethylene), poly (4,4'-isopropylene-diphenylene carbonate), poly(ethylene-vinyl esters), poly(ethylene-vinyl acetate), poly(vinyl chloride-diethyl fumarate), poly(esters of acrylic and methacrylic), cellulose acetate, cellulose acylates, partially hydrolyzed poly(vinyl acetate), poly(vinyl butyral), poly(amides), poly(vinyl carbonate), poly(urethane), poly(olefins), and the like. These polymers and their physical properties are known to the art and they can be synthesized according to the procedures disclosed in *Encyclopedia of Polymer Science and Technology*. Vol. 15, pp 508–30, (1971), published by Interscience Publishers, Inc., New York; Polymers Vol. 17, pp 938–56, (1976); *Technical Bulletin SCR*-159. (1965), Shell Corp., New York, and the references cited therein; and in *Handbook of Common Polymers*. by Scott and Roff, (1971) published by CRC Press, Cleveland, OH.

The vaginal drug delivery dispenser as provided herein can be manufactured from porous and microporous tubing made from polymers that can be melt-extruded to form a tubular structure. In one process a tube is produced from an extrudable polymeric composition by extruding it, with a commercial extruder, through a die, a polymer that includes a leachable additive of pre-poreforming size. Typical examples of leachable components are water soluble modified starches and other water soluble polymers such as polyethylene oxides, polyethylene glycols, polyvinyl alcohol, sodium alginate, gelatin, hydroxyethyl cellulose, and the like. Leachable components also can be salts such as NaCl, KCl, NaHCO$_3$, Na$_2$CO$_3$, HaHPO$_4$, etc., or low molecular weight organic compounds such as urea, sorbitol, mannitol, lactose, fructose, etc. Pores formed of controlled porosity by leaching a leachable element from the wall of a dispensing device are known to the prior art in Ayer et al., U.S. Pat. No. 4,200,098 and in Ayer et al., U.S. Pat. No. 4,285,987.

In another process a polymer and a leachable sintered powder are mixed and extruded through a die of known shape and dimensions. A representative sintered powder is prepared by blending, for example, hydroxypropyl cellulose and polyethylene glycol, followed by sintering the blend in a high speed mixer at an elevated temperature. Next a polymer and the powder are ground in a conventional grinder to a known sieve size. The blend is then extruded and after extrusion the tube is subjected to intensive leaching or washing to produce a porous structure in the tube wall. Another process for forming a porous tube comprises extruding, in an extruder of a conventional type operated at a pressure needed for extrusion, a polymer and a blowing agent. Typical blowing agents that also create a foamed or a porous cellular structure are represented by aryl-bissulfo-hydrazide, azodicarbonamide, azobisisobutyronitrile, ammonium sesquicarbonate, and the like. The blowing agent releases gas and expands when the tube is exposed to a heat zone, which physical action and evolution of gas forms the porous structure. Procedure, equipment and materials suitable for manufacturing porous and microporous structures are known to the art in Raley U.S. Pat. No. 3,233,761; in Yamamoto et al., U.S. Pat. No. 3,551,538; in Thomas U.S. Pat. No. 3,552,658; in Saito et al, U.S. Pat. No. 3,911,072 and in Youval et al, U.S. Pat. No. 4,182,582.

The porous polymeric material further can be described as having pores that can be characterized as continuous pores interconnected through tortuous paths of regular and irregular shape. Generally the final porous materials can possess from 5% to 95% of a pore former comprising a pore size that permits the controlled release of the drug. Generally a pore size of from 10 angstroms to 200 microns, or more, can be used for releasing the agent with the pores filling with a carrier present in the device, or found in an environment of use, that enters the pores through which the agent migrates to the exterior of the dispenser. Materials useful for making porous tubing include the polymers described above and polymers such as polycarbonates, polyacrylonitrile, synthetic or natural rubbers, block copolymers such as styrene butadiene, styrene acrylonitrile, triple-block rubbers, polyhexamethylene adipamide, polyolefins, polyalkylene sulfide, polyethers, polyesters, polycellulose, acylates, and like porous homopolymers, copolymers, and terpolymers.

Exemplary inner mass transfer carrier 15 includes carriers that are suitable for housing drug 14 in reservoir 13, including solid, liquid, semi-liquid carriers, and the like, such as emulsions, gels, glycols, and the like. These carriers are permeable to the passage of drugs, they are capable of containing dissolved and undissolved drugs, and they are capable of forming a carrier wall interface at the inner surface of wall 12, or wall 19, such as a solid or a liquid carrier wall interface at the inner surface of wall 12 or wall 19. Typical carriers include a member selected from the group consisting of mineral, animal, fruit, nut, plant, sylvan, inorganic and organic oils. The carriers also include a member selected from the group consisting essentially of liquids, glycols, alkylene glycols, dialkylene glycols, poly(alkylene glycols), poly(oxyalkylene) copolymer, aqueous gels, and the like. The carriers also include aqueous carriers such as water, saline, and buffers. Representative of carriers include vegetable oil, aqueous media such as water mixed with poly(alkylene glycols) including poly(ethylene glycols) having a molecular weight of 400 to 6000, poly(propylene glycol) having a molecular weight of 500 to 2000, glycerol polysorbate 80, and the like. Representative solid carriers useful as the inner mass transfer conductor include gelatin, collagen, sodium alginate, gum tragacanth, and the like. The solid carrier in the reservoir also can be a thermo-setting organopolysiloxane that is vulcanized with a peroxide curing catalyst such as benzol peroxide, di-p-chlorobenzol peroxide, and the like, at temperatures of about 200° C. and requiring a subsequent heat treatment. The solid carrier can be a hydroxyl terminated organopolysiloxane, commonly known as room temperature vulcanizing elastomer polymers, RTV, which harden to carrier elastomers at room temperature after the addition of cross-linking agents in the presence of curing catalysts. Representative catalysts are metallic salts of carboxylic acids, such as tin salts, tin octoate, tin ethylhexanoate, and the like. The inner reservoir carrier also can embrace a single component silicon rubber composition cured at room temperature. The single component compositions primarily contain organopolysiloxanes with two terminal hydrolyzable acyloxy groups, such as an acetoxy group. The acyloxy groups are hydrolyzed to form trifunctional siloxane which cross-link the polymer into a cured carrier. The carrier can be formed also of a two component dimethylpolysiloxane composition, platinum catalyzed at room temperature or at slightly elevated temperature and capable of additional cross-linking. Silicone polymers are known in U.S. Pat. Nos. 2,541,137; 2,723,966; 2,863,846; 2,890,188; 2,927,907; 3,022,952, and 3,035,016; and Great Britain Pat. Nos. 798,669 and 804,199. Carriers also are known to the art in *Pharmaceutical Sciences,* by Remington (1970), published by Mack Publishing Company, Easton, Pa.

The phrase, "beneficial agent," as used herein, denotes vaginally administrable physiologically active or pharmacologically active substances that produce a local or systemic effect when released in the biological vaginal environment. The useful active agents can be inorganic, or organic, a drug, a spermicide, a hormone, and the like.

The terms, "spermicide and spermicidal," as used herein, are intended to encompass agents that kill sperm, as well as those agents which immobilize or render sperm ineffective for their intended effect by spermicidal-semen contact. In one embodiment the spermicides include anionic surface active spermicides, non-ionic surface active spermicides and cationic surface active spermicides, and mixtures thereof. Exemplary spermicides that can be released by vaginal dispenser 10 are represented by the following: di-isobutyl-phenoxypolyethoxy ethanol, dodecaethylene glycol monolaurate p-methanylphenyl polyoxyethylene, methoxypolyoxyethylene glycol laurate, nonylphenoxypolyethoxy ethanol, polyethylene glycol of monoisooctyl phenol ether, polyoxyethylene-nonyl phenol, polyoxyethylene nonylphenol ether, aminopropanesulfonate, nonylphenol nonaethoxylate, tri-isopropyl-phenoxypolyethoxy ethanol, sodium lauryl sulfate, glyceryl monoricinolate, spermicidal mixtures such as methoxypolyethylene glycol laurate and nonylphenoxypolyethoxy ethanol, trioxymethylene and nonylphenoxypolyoxyethylene ethanol, p-tri-isopropyl phenoxypolyethoxyethanol and sodium lauryl sulfate, p-di-isobutyl phenoxypolyethoxyethanol and nonylphenoxypolyethoxyethanol, sodium sulfodioctyl succinate and tri-isopropylphenyloxypolyethoxyethanol, glyceryl monoricinoleate and tri-isopropylphenyloxypolyethoxyethanol, and the like. The amount of spermicide in vaginal device 10 can be up to 100%. The amount of spermicide in the device when the spermicide is mixed with a mass transfer conductor is about 0.4% to 80% by weight of the total ingredients in the vaginal dispenser. The dispenser, when in operation, releases a spermicidally effective amount of spermicide over time, and more particularly from 50 microns to 500 milligrams per hour, or higher. The dispenser releasing the spermicide can be positioned in the vagina prior to intercourse, and removed in a period of time after intercourse, or the device can be inserted and maintained in the vagina for several days up to a month.

Vaginal dispenser 10 can be used for the control of ovulation, or the prevention of pregnancy by suppressing ovulation, by administering contraceptive hormones. The contraceptive hormones useful for this purpose include progestational and estrogenic hormones. These hormones, when released into the vagina, are absorbed into the body and are thought to prevent conception by inhibiting the release of luteninizing hormone-releasing factor from the hypothalmus. This physiological action prevents the follicle to grow, and it also prevents the luteninizing hormone from triggering ovulation. The contraceptive hormones that are used for the program of the invention include broadly antifertility steroids that can be used for regulating the fertility or ovulatory cycle in females of reproduction age. The contraceptive hormones include progestational and estrogenic steroids.

The administration of a contraceptive hormone, or the administration of a combination of contraceptive hormones in the vagina for entry into the systemic circulation, which act primarily through the mechanism of gonadotropin suppression due to the progestational and the estrogenic activities of the steriods, with the resulting inhibition of ovulation, can be effected by the programs provided by the invention. One program for administering the naturally occurring steroid progesterone to the vagina can be generically described as three-weeks-on and one-week-off programs. The program comprises the steps of (1) inserting the vaginal dispenser into the vagina on the fifth day of the menstrual cycle, counting the first day of bleeding as day one, (2) retaining the system in the vagina for 20 to 21 days, preferably for three weeks, (3) administering from 1 microgram to 500 micrograms of progesterone to the vagina daily, preferably into the vaginal fluid during the three week period, (4) removing the system from the vagina for one week, with no progesterone delivered during this period, and (5) repeating the contraceptive program at the end of this latter period by inserting a new delivery system into the vagina. The contraceptive program that can be used for the management of the ovulatory cycle comprises delivering progesterone to the vagina for one week from the fifth day to the twelfth day of the intermenstrual period. The system is positioned in the vagina beginning with day five of the menstrual period, counting the first day of bleeding as day one.

The contraceptive programs for delivering progestins to the vagina comprise delivering the hormonal steroid to the vagina, preferably to the vaginal mucosa, at the rate of 1 microgram to 10,000 micrograms a day. The contraceptive programs presently preferred are the three-weeks-on and one-week-off programs, and the fifth to the twelfth day intermenstrual period programs as described above. The progestins include norethindrone, norethynodrel, norgestrel, and the like. The contraceptive programs provided by the invention also include delivering a combination of progestational and a estrogenic steroid to the vaginal environment. The program comprises inserting the vaginal dispenser into the vagina for releasing from 0.1 micrograms to 10,000 micrograms (mcg) each at a continuous rate for three weeks of the four week cycle, or by using a program that corresponds to the oscillatory pattern exhibited by the normal ovarian cycle. Representative combinations that can be simultaneously released from the system include natural estrogen and natural progesterone; 35 mcg/day of ethenyl estradiol and 0.5 mg/day of norethindrone; 50 mcg/day of ethyinyl estradiol and 1.0 mg/day of ethynodiol diacetate; 75 mcg/day of mestranol and 5.0 mg/day of norethyndrel; 30 mcg/day of ethinyl estradiol and 0.3 mg/day of norgestrel; 50 mcg/day of ethinyl estradiol and 0.5 mg/day of norethindrone; 80 mcg/day of mestranol and 1.0 mg/day of norethindrone; 50 mcg/day of estrogen and 0.1 mg/day of progesterone; 100 mcg/day of estrogen and 0.4 mg/day of norethindrone; 40 mcg/day of estrogen and 0.5 mg/day of norgestrel, and the like. The vaginal dispenser houses from about 2 mcg to 7.5 grams of estrogenic steroid and about 0.2 mg to 7.5 grams of progestational steroid alone or in combination. The abbreviation "mcg" indicates microgram and "mg" indicates milligram and "/day" indicates the rate of delivery per day. Generally the progestational or estrogenic contraceptive steroid will be released at the rate of 0.05 micrograms to 50 milligrams per day, excluding the specific contraceptive programs set forth above. The steroids are know in *Remington's Pharmaceutical Sciences*, 14th Ed., (1970), published by Mack Publishing Co., Easton, Pa, and the Pharmacological Bias of Therapeutics, by Goodman and Gilman, 4th Ed., (1970), published by MacMillan Company, London.

Vaginal dispenser 10 also can be used for estrogen replacement therapy, as related to ovarian functions. The cessation of ovarian function during middle life is a physiological event. It is medically accepted this event is the basis of the menopausal period. The menopausal period does not happen all at once, and this critical period of life that occurs in women is often referred to as the climacteric. The menopausal period is characterized by menopausal symptoms initiated by a decrease in estrogen secretion, which follows the cessation of cyclical ovulation and menstruation. The menopausal symptoms generally include hot flashes, fatigue, insomnia, obesity, wrinkles and emotional libility, and the postmenopausal osteoporosis or bone deterioration. It is generally recognized estrogen therapy and estrogen in conjunction with progestin therapies, is useful for the management of the climacteric. The vaginal dispenser provided by the invention makes available a method useful for relieving or preventing menopausal, perimenopausal and postmenopausal symptoms. The steroid administered for tis purpose can be administered in estrogenic effective amounts continuously or in interrupted patterns. The estrogenic steroid can be administered with progestational steroids continuously or in an interrupted pattern. The method additionally comprises administering the steroid in a cyclical pattern or in a sequential pattern. The cyclical pattern comprises administering the estrogenic steroid for three weeks out of four weeks. The sequential pattern comprises administering an estrogenic steroid with added progestational steroid. The sequential program comprises (1) estrogenic steroid for 11 days then estrogenic steroid and progestational steroid for 10 days followed by 7 steroid-free days; (2) estrogenic steroid for 15 days followed by estrogenic and progestational steroid for 13 days; (3)

estrogenic steroid for 14 days and then estrogenic steroid and progestational steroid for 7 days followed by 7 steroid-free days; (4) continuous estrogenic steroid and progestational steroid for 5 to 7 days; and, (5) continuous estrogenic steroid and progestational steroid for 5 to 7 days followed by at least one repeated program.

The invention also provides a method for treating and lessening the incidence of endometrial hyperplasia. The method comprises administering a steroid intravaginally in a cyclical pattern, or in a sequential pattern. The cyclical pattern comprises administering low doses of an estrogenic steroid for three weeks of a four week period. Typical steroids that can be administered in a therapeutically effective amount for lessening the incidence of hyperplasia and for substantially maintaining normal endometrium include estrogen sulphate, estradiol valerate, conjugated equine estrogens, estriol hemisuccinate, and the like. The sequential patterns comprise administering an estrogenic steroid intravaginally for (a) estrogen for 11 days then estrogen and progestational steroid for 10 days, then 7 steroid free days; (b) estrogenic steroid for 15 days and estrogenic steroid and progestational steroid for 13 days; (c) estrogenic steroid for 14 days and then estrogenic steroid with a progestational steroid for 7 days followed by 7 days without any steroid; (d) estrogenic steroid and progestational steroid for 5 to 7 days; (e) estrogenic steroid daily for at least 7 days with progestational steroid administration accompanying at least 5 of said days, and (f) estrogenic steroid for days 1 to 25 with progestational steroid added for at least 5 days, usually from day 16 to 25. Sequential therapy also is indicated for lessening the incidence of abnormal vaginal bleeding in patients prone to same. For sequential therapy the amount of estrogenic steroid administered per day is from 50 mcg to 1.5 g, and the amount of progestational steroid administered daily is from 50 mcg to 1.5 g.

The term, "progestational steroid," as used herein, embraces progestogen, which term is used in the pharmaceutical art to generically describe steroids possessing progestational activity. The progestational steroids further include naturally occurring steroids and synthetic steroids known as progestins. Exemplary progestational steroids include progesterone or pregn-4-ene-3,20-dione; 17 alphahydroxy-progesterone or 17 alpha-hydroxypregn-4-ene-3,20-dione; 17 alpha-hydroxy-progesterone-3-cyclopentyl enol; medrogestone or 6,17-dimethylpregna- 4,6-diene-3,20-dione; medroxyprogesterone or 17 alphahydroxy-6 alpha-methylpregn-4-ene-3,20-dione; megestrol acetate or 17 alpha-hydroxy-6-methylpregna-4,6-diene-3,20-dione acetate; chlormadinone acetate or 6-chloro-17-alpha-hydroxy-pregna-4,6,diene-3,20-dione acetate; allylestrenol or 17-(2-propenyl)estr-4-en-17-ol; ethynodiol or 19-nor-17 alpha-pregn-4-en-20-yne-3 beta,17-diol; ethynodiol diacetate; lynestrenol or 19-nor-17 alpha-pregn-4-en-20-yn-17-beta-ol; norethindrone or 17-hydroxy-19-nor-17 alpha-pregn-4-en-20-yn-3-one; norethynodrel or 17-hydroxy-19-nor-17 alpha-pregn-5(10)-en-20-yn-3-one; norgestrel or 13-ethyl-17-hydroxy-18,19-dinor-17 alpha-pregn-4-en-20-yn -3-one; norgesterone or 17-hydroxy-19-nor-17 alpha-pregna 5(10),-20-dione-3one; quingesterone or progesterone cyclopentyl-3-enol ether; and other progestins such as norvinesterone; levonorgestrel; oxogestone; oxogestone phenpropionate; norethisteron; tigestol, and the like.

The estrogenic hormones used for controlling the ovulatory cycle include estradiol or estra-1,3,5(10-triene-3,17 beta-diol; estradiol 3-benzoate; estradiol 3-acetate; estradiol 3,17-diacetate; estriol or estra-1,3,5,(10)-triene-3,16 alpha-17 beta-triol; estrone or 3-hydroxy-estra-1,3,5(10)-trien-17-one; ethinyl estradiol or 19-nor-17 alpha-pregna-1,3,5(10)-trien-20-yn-3,17-diol; mestranol or 3-methoxy-19-nor-17 alpha-pregna-1,3,5(10)-triene-20-yn-1-7-ol; quinestradiol or 3-(cyclophentyloxy)-estra-1,3,5(10)-trient-16 alpha-17 beta-diol; quinestrol or 3-(cyclopentyloxy)-19-nor-17 alpha-pregna-1,3,5(10)-trien-20-yn-17-ol; and other estrogens, such as estrazinol; estrofurate; conjugated estrogens; conjugated equine estrogens; micronized estradiol; esterified estrogens; piperazine estrone sulfate; estriol hemisuccinate; estrogen sulphate; estrone, and the like.

Additionally the above progestational and estrogenic agents can be in the form of their pharmacologically accepted derivatives, such as their hydroxy or keto groups can be in a derivative form for the present purpose. The progestational or estrogenic derivative used should easily convert to the active agent upon its release from the device by biological activities such as enzymatic transformation, pH assisted hydrolysis in the vagina, tissue and metabolism, and the like. The derivative also can be used to control the solubility of the agent in the carrier core and to assist in metering the agent from the device. Suitable derivatives include, without limitation, esters with pharmaceutically acceptable acids such as acetate, glucuronate, benzoate; propionate, butyrate, valeroate, hexanoate, heptanoate, maleate, citrate, succinate, tartrate, fumarate, maleate, ascorbate, sulphate, phosphate, and the like; ethers such as lower alkoxy-tetrahydropyran-yl, unsubstituted tetrahydropyran-yl, silyl moieties, trifluoromethloxy, cyclopentylenol ethers and other functional groups such as ureido, and the like.

In one manufacture provided by the invention the two ends joined in unity to define and form the vaginal dispenser can be held one within the other in fluid tight relation by solvent bonding, by adhesive joining, by heat fusing, by heat bonding, by pressure, and the like. When a solvent is used the inside surface of one tube end that acts as a female member and the outside surface of the other end that acts as a male member are moistened with an organic solvent to cause the surfaces to feel tacky and when placed in contact the surfaces are bonded and adhere in a fluid tight union. The needs of the tube forming the body of the dispenser can be adhesively united to form a closed dispenser by applying an adhesive to the exterior surface of one end of the tube and then slide the end into and against the inside surface of the other end. For the above procedures the solvents include organic solvents such as methylene chloride, ethylene dichloride, trichlorobenzene, dioxan, isophorne, tetrahydrofuran, aromatic and chlorinated hydrocarbons; mixed solvents such as 50/50 ethylene dichloride/diacetone alcohol; 40/60 alcohol/toluene; 30/70 alcohol/carbon tetrachloride, and the like. Suitable adhesives include natural adhesives and synthetic adhesives such as animal, nitrocellulosic, polyamide, phenolic, amino, epoxy, isocyanate, acrylic, silicate, organic adhesives of polymers, and the like. The adhesives are known to the art in *The Encyclopedia of Chemistry*, 2nd Ed., edited by George L. Clark and Gessne G. Hawley, (1966), published by VanNostrand Reinhold Co., Cincinnati, OH; and the solvents are known in *Encyclopedia of Chemical Technology*, Kirk-Othmer, 2nd Ed., Vol. 16, (1969), published by Interscience Publishers, Inc., New York.

An intravaginal dispenser used for the purpose of this invention is manufactured as follows: First, a section of styrene-butadiene block copolymer vaginally acceptable tubing is washed with distilled water for 45 to 60 hours, then dried in air at room temperature. Then the tubing is cut into appropriate lengths and shaped like a ring, as seen in FIG. 1, and molded into a torus at 165° C. Next, one end is enlarged by inserting a heated mandrel, cooled, and the outside of the other end of the tube very lightly dampened with methylene chloride and inserted into the female end for joining the opened tube at its ends, thereby forming a closed vaginal dispenser. Next, the hollow ring is filled by injecting a steroid carrier mixture into the reservoir through a tube piercing inlet port pushed through the wall of the dispenser, with continuous filling of the reservoir until all the air is displaced through a tube piercing exit port also pushed through the wall of the dispenser. This procedure fills the reservoir. Finally, the piercing ports are removed and the puncture points are sealed with a little methylene chloride. The reservoir is filled with progesterone in polyethylene glycol having a molecular weight of 400, at 5% wt/wt.

The procedure described above is repeated for preparing a vaginal dispenser having a toroidal shape and made with the same copolymer. The dispenser is manufactured from a length of clean tubing having a first end resiliently expanded for receiving the second end in a sealingly engaging relation to form a closed reservoir dispenser. The dispenser is made with a wall having a thickness of 1.78±0.08 mm, and internal diameter of 6 mm, and an outside diameter of 4.4 cms, and a reservoir containing 35% progesterone and 65% polyethylene glycol having a molecular weight of 600.

A vaginal dispenser useful for releasing a spermicide is manufactured as follows: First, a 16.5 mm length of a microporous cellulose tubing having a thickness, when dry, of 25 microns, and a thickness, when wet, of 50 microns is shaped like a ring. Then one end is permanently enlarged and the other end moistened with methylene chloride and the regular end inserted into the enlarged end, thereby joining the tube into a closed vaginal dispenser comprising a microporous wall surrounding and defining an internal, hollow reservoir. Next, the reservoir is filled by injecting into the reservoir nonylphenoxypolyethoxy ethanol, 30% by weight, in an aqueous carrier.

It will be understood to those versed in the art in the light of the present specification, drawings and accompanying claims that the invention makes available to the art both a novel and useful vaginal device for delivering agents such as progestational and estrogenic steroids to produce a desired anti-fertility effect; and spermicides for their effects; the rate of release from these devices can be controlled to produce this effect, while simultaneously contributing to the dispensing art. It will be further understood to those versed in the art that different embodiments of this invention can be made without out departing from the spirit and the scope of the invention. Accordingly, it is to be understood the invention is not to be construed as limited, but embraces all equivalents inherent herein.

I claim:

1. A method for administering an estrogenic composition for estrogen replacement in a woman exhibiting a decrease in estrogen secretion, and for administering a progestational composition for the management of endometrial hyperplasia in said woman, which method comprises:
   (a) placing in the vagina of said woman a vaginal dispenser adapted and shaped for easy placement and comfortable retention in the vagina, the dispenser comprising:
      (1) a multiplicity of tubes with each tube comprising a wall that surrounds an internal space, said wall comprising a member selected from the group consisting of olefin, vinyl, condensation, addition and rubber diffusion and microporous polymers;
      (2) a composition in the internal space, said composition comprising about 2 mcg to 7.5 g of an estrogenic steroid, pharmaceutically acceptable mass transfer carrier for said steroids;
   (b) administering the estrogenic steroid through the wall from the dispenser into the vagina in a therapeutically effective amount for replacing the estrogen in said woman; and,
   (c) administering the progestational steroid through the wall in a therapeutically effective amount from the dispenser for substantially lessening endometrial hyperplasia in said woman.

2. A method of estrogen replacement for a woman in need of estrogen replacement, and for progestin management of endometrium hyperplasia responsive to a progestin in said woman, which method comprises:
   (a) placing in the vagina of said woman a dispenser comprising:
      (2) at least one tube comprising a wall composition that surrounds an internal lumen, said wall composition vinyl, condensation, and addition polymer that releases a steroid by passage through micropores in the wall, which micropores are formed by leaching a pore former from the wall, said dispenser adapted and shaped for easy placement and comfortable retention in the vagina;
      (2) a pharmaeutically acceptable carrier in the lumen, said carrier comprising a member selected from the group consisting of solid, liquid and semi-liquid carriers and comprising up to 7.5 g of dissolved and undissolved estrogen and progestin steroids;
   (b) administering the estrogen steroid from the dispenser through micropores in the wall into the vagina in a therapeutically effective amount for at least five days for replacing estrogen in said woman; and,
   (c) administering the progestin steroid from the dispenser through micropores in the wall into the vagina in endometrium hyperplasia in said woman.

* * * * *

UNITED STATES PATENT AND TRADEMARK OFFICE
CERTIFICATE OF CORRECTION

PATENT NO. : 4,961,931

DATED : October 9, 1990

INVENTOR(S) : Patrick S.-L. Wong

It is certified that error appears in the above-identified patent and that said Letters Patent is hereby corrected as shown below:

Claim 1, in column 12, in line 22, after "steroid," insert --about 0.2 mg to 7.5 g of a progestational steroid, and a--;

Claim 2, in column 12, in line 38, "(2)" should read --(1)--;

Claim 2, in column 12, in line 40, after "composition" insert --comprising a member selected from the group consisting of an olefin,--;

Claim 2, in column 12, in line 46, "pharmaeutically" should read --pharmaceutically--;

Claim 2, in column 12, in line 59, after "in", first appearance, insert --therapeutically effective amount for the management of the--.

Signed and Sealed this

Seventh Day of January, 1992

Attest:

HARRY F. MANBECK, JR.

Attesting Officer      Commissioner of Patents and Trademarks